US011478207B2

(12) United States Patent
Simon et al.

(10) Patent No.: US 11,478,207 B2
(45) Date of Patent: *Oct. 25, 2022

(54) METHOD FOR VISUALIZING A BONE (71) Applicant: Stryker European Operations Holdings LLC, Kalamazoo, MI (US)

(72) Inventors: Bernd Simon, Kiel (DE); Arno Blau, Balingen (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 9 days.

This patent is subject to a terminal disclaimer.

(21) Appl. No.: 17/090,348

(22) Filed: Nov. 5, 2020

(65) Prior Publication Data

US 2021/0121147 A1 Apr. 29, 2021

Related U.S. Application Data

(63) Continuation of application No. 16/326,071, filed as application No. PCT/US2016/047487 on Aug. 18, 2016, now Pat. No. 10,827,998.

(51) Int. Cl.
*A61B 6/00* (2006.01)
*G06T 7/13* (2017.01)
(Continued)

(52) U.S. Cl.
CPC ............ *A61B 6/505* (2013.01); *A61B 6/4441* (2013.01); *A61B 6/466* (2013.01); *A61B 6/487* (2013.01); *A61B 6/5217* (2013.01); *A61B 6/5223* (2013.01); *A61B 6/583* (2013.01); *A61B 6/584* (2013.01); *G06K 9/628* (2013.01); *G06T 7/13* (2017.01); *G06T 15/08* (2013.01); *G06T 19/20* (2013.01); *A61B 6/5205* (2013.01); *A61B 2090/367* (2016.02); *A61B 2090/376* (2016.02);
(Continued)

(58) Field of Classification Search
CPC ....... A61B 6/505; A61B 6/466; A61B 6/5205; A61B 2090/367; G06T 7/13; G06T 15/08; G06T 19/20
See application file for complete search history.

(56) References Cited

U.S. PATENT DOCUMENTS 8,685,034 B2 4/2014 Giersch et al.
2007/0219445 A1 9/2007 Liebschner et al.
(Continued)

FOREIGN PATENT DOCUMENTS

WO 2012112694 A2 8/2012

OTHER PUBLICATIONS

International Search Report for Application PCT/US2016/47487 dated Oct. 27, 2016.

*Primary Examiner* — Said Broome
(74) *Attorney, Agent, or Firm* — Lerner, David, Littenberg, Krumholz & Mentlik, LLP (57) ABSTRACT

A method and a corresponding system are provided. The method comprises steps of providing 2D images and subsequently detecting outlines of a primary structure in each of the images. A visual representation of the 2D images is generated and the 2D images are then arranged as 2D slices in a 3D visual representation. To this end, at least two of the 2D images are taken at different imaging angles. The method provides a 3D visual representation of a region of interest comprising a primary structure to support a spatial sense of a user.

18 Claims, 6 Drawing Sheets

(51) Int. Cl.
  *G06K 9/62* (2022.01)
  *G06T 15/08* (2011.01)
  *G06T 19/20* (2011.01)
  *A61B 90/00* (2016.01)

(52) U.S. Cl.
  CPC ............ *A61B 2090/3966* (2016.02); *G06T 2207/10116* (2013.01); *G06T 2207/30008* (2013.01); *G06T 2207/30052* (2013.01); *G06T 2207/30204* (2013.01); *G06T 2219/2016* (2013.01); *G06V 2201/033* (2022.01)

(56) References Cited

U.S. PATENT DOCUMENTS

| | | | |
|---|---|---|---|
| 2008/0033240 A1* | 2/2008 | Hoffman | A61B 34/10 600/109 |
| 2012/0172700 A1* | 7/2012 | Krishnan | G16H 30/20 600/407 |
| 2013/0166256 A1 | 6/2013 | Wirx-Speetjens et al. | |
| 2016/0070436 A1* | 3/2016 | Thomas | G06T 19/003 715/771 |

\* cited by examiner

METHOD FOR VISUALIZING A BONE

CROSS-REFERENCE TO RELATED APPLICATIONS

This application is a continuation of U.S. application Ser. No. 16/326,071, filed on Feb. 15, 2019, which is a national phase entry under 35 U.S.C. § 371 of International Application No. PCT/US2016/047487, filed on Aug. 18, 2016, published in English, the disclosures of which are incorporated herein by reference.

BACKGROUND OF THE INVENTION

The invention relates to the field of computer based assistance of surgery. In particular, the invention relates to a method of automatic image processing including 3D visualization for supporting a spatial sense of a user. The method may be implemented as a computer program executable on a processing unit of a suitable device.

In every surgery where intraoperative imaging is used it is a challenge to accurately perform the necessary steps of a procedure of treating a bone fracture. Usually, almost each step requires an iterative process based on several X-ray images. A significant radiation exposure is thus produced. The amount of radiation may be highly depended on the know-how and skill of the physician.

Some imaging systems may provide 3D visual representations of a surgery area or a region of interest, such as a region comprising a bone fracture. Such 3D visual representations may contain valuable information about the current spatial position of an implant in relation to a bone and/or one or several bone fragments. Based on the information a surgeon may determine the next surgery steps or may determine the need of further (re)positioning of the implant. 3D visual representations of a region of interest often rely on several 2D images, which on the one hand often requires enhanced radiation exposure of a patient and on the other hand causes enhanced computational expense.

Accordingly, there may be need for an improved assistance during a surgical procedure.

BRIEF SUMMARY OF THE INVENTION

It may be seen as an aspect of the invention to provide a method and device for more efficiently assisting in performing a surgical procedure. It would be highly beneficial to reduce the amount of radiation to which a patient—as well as a surgeon—is exposed during a surgical procedure, to reduce computation time needed for providing visual representations of a surgical area or region of interest, and/or to more efficiently visually represent relevant information on the surgical site to the surgeon.

The mentioned aspects are solved by the subject-matter of each of the independent claims. Further embodiments are described in the respective dependent claims.

According to a first aspect of the invention, a method for visualizing a bone, for instance a femur or a hip bone, is provided. The method comprises the step of providing 2D images of the bone, wherein at least two of the 2D images are taken at different imaging angles. In a further method step, outlines of a primary structure are detected in the 2D images. Based on the outlines, a visual representation of the 2D images is subsequently generated. Finally, a visual representation of the 2D images is arranged in form of 2D slices in a 3D visual representation. Thereby, the arrangement of the 2D slices in the 3D visual representation is based on the different imaging angles under which the 2D images are taken. A purpose of the 3D visual representation can be seen in supporting a spatial sense of a user. By "spatial sense of a user" it is meant that a person viewing the image can determine the location and orientation of a bone, bone fragment or implant from spaced 2D slices forming a partial 3D visual representation of the imaged region based on the user's prior knowledge.

The 2D images may be X-ray images, ultrasound-images, images taken with magnetic resonance imaging or taken with any other imaging method. The method relies on provision of at least two 2D images taken from different angles. Accordingly, also a plurality of more than two 2D images taken from a plurality of more than two angles may be provided and processed within the method. The arrangement of the 2D images as 2D slices in a 3D visual representation may, for instance, be conceived as 2D pages of an opened book. More generally, the arrangement of the 2D images as 2D slices in a 3D representation may be conceived as intersecting 2D planes in a 3D image space. The arrangement of the 2D planes in the 3D space corresponds to the angles under which the corresponding 2D images are taken, respectively.

2D images can be taken from different angles, for instance when an image is taken with a C-arm imaging device and the C-arm is then rotated and another image is taken. It is preferred within the invention that the angles under which different 2D images are taken are larger than 10°, respectively. More preferably, the angles under which different 2D images—which are subsequently provided within the method—differ by at least 15°, or differ by more than 30°. This helps to make sure that the 2D slices given in the 3D visual representation are inclined by those angles relative to each other, such that feature/parts of objects comprised in the 2D slices sufficiently differ from each other. If the angles would be too close to each other, the features/parts of objects depicted in corresponding 2D slices would be similar and not of much support for a spatial sense of a user, who wants to reconstruct with his spatial sense a full 3D view of a region of interest.

The 3D visual representation according to the invention differs from conventional 3D representations in that the 3D visual representation is built from a collection of at least two 2D planes—or more generally 2D surfaces—and the space in between the respective 2D surfaces is left empty. Thus as few as two 2D planes can provide sufficient input for a user to determine essential information about the imaged region. Each 2D surface contains image information of the considered region of interest according to a specific angle or perspective and a specific 2D layer or level of the region of interest. In the 3D visual representation, the at least two 2D surfaces are arranged according to the angles or perspectives and the position of the respective layer of the region of interest. For example, a 3D visual representation according to the invention can be imagined as a collection of intersecting and/or parallel arranged 2D planes in 3D position space. Corresponding image information is comprised on the 2D planes, respectively. The remaining space between the 2D planes is left empty, i.e. no image information is provided or given for this space.

In other words, the invention relates to a method for automated generation of a grid model of a bone. The invention does not provide a full 3D image reconstruction of a bone or a region of interest, but provides essential information on the bone or region of interest comprised in 2D slices, which map parts of the full 3D region of interest. In this way, computational costs for full 3D image reconstruction can be reduced. At the same time, the spatial sense of a user can be stimulated to reconstruct the full or essential parts of the 3D information, such that the necessary or important information is available due to a combination of the provided reduced 3D visual representation and the spatial sense and experience of a user.

According to an embodiment of the invention, a primary structure in the 2D images may be given by at least one of a bone, and a bone fragment.

According to an embodiment of the invention, a primary structure in the 2D images may be given by at least one of an implant, and a reference body.

A reference body may comprise a plurality of fiducial members or markers, most preferably at least three such markers that are visible to an imaging system, which is used to provide the 2D images. It may further be preferred that the fiducial markers comprise spheres that are visible to the imaging system. The reference body may be used in determining a spatial dimension and position of an implant. For example, an implant may include the reference body or may be positioned in a predefined location in relation to the reference body. Both the reference body and the implant are detected or recorded in an image, for instance an X-ray or fluoro image. By means of the correct identification and registration of the reference body—in particular the preferably comprised fiducial markers—, the actual spatial dimension and position of the implant can then be determined.

The reference body may be directly attached to an anatomical structure, e.g. may be in contact with an outer surface of a body part of interest. The reference body may also be indirectly coupled to an anatomical structure, for example via a handling tool for inserting an implant. On the other hand, the reference body may be at least a part of an implant. In other words, an implant which is adapted to be fixed at or in a bone may comprise elements which can be identified in an image of the bone or at least a section of the bone so that geometrical aspects may be determined based on the identified elements. For example, the elements may define points so that two elements may define a line or an axis, or the elements may define a contour so that a centre axis may be determined.

Further, the reference body may be integrated into an aiming device for, e.g. supporting an insertion of a locking screw through a bore in a leading end of a bone nail, wherein the aiming device may be adapted to be coupled to a handling tool for inserting the bone nail. Therefore, the aiming device may be adapted to be coupled to a trailing end of the bone nail and may extend outside the body of a patient as far as the bone nail extends inside the bone so that at least a portion of the aiming device can be visible in an image of the section of the bone including the leading end of the bone nail. Such an aiming device is described and shown in U.S. Pat. No. 8,685,034, the disclosure of which is incorporated herein by reference.

As used herein, the term "anatomical structure" refers to anything at a bone and in particular to a geometrical aspect of a bone, i.e. a point, a line, an arc, a centre point, an axis, a cylinder surface, a ball surface, or the like. For example, a geometrical aspect of a femur may be the outer surface of the femur head, an axis defined by the neck between shaft and femur head, a longitudinal axis of the femur shaft, a most distal point on the bone surface, a line defined by the centre points of the condyles, or a line defined by the most posterior points at the condyles. It will be understood that the other bones provide other and/or comparable suitable geometrical aspects.

According to a further embodiment of the invention, the method further comprises the step of detecting at least three markers in the 2D images. Thereby, a marker may be a reference body or a part of a reference body, an implant or a bone shape. For instance, a marker may be a radiopaque sphere, which is part of a reference body attached to an implant. In a further method step a spatial arrangement of the primary structure based on the position of the at least three markers can be determined. The arrangement of the 2D images as 2D slices in the 3D visual representation is then based on the determined spatial arrangement.

According to an embodiment of the invention, the method further comprises the step of classifying the primary structure into a class of implants, a class of bones, a class of bone fragments and/or a class of reference bodies. The method-step of arranging the visual representation of the 2D images in form of 2D slices in the 3D visual representation may then be based on the classification of the primary structure.

For instance, primary structures corresponding to different classes—for example corresponding to a class of implants and a class of bones—may be represented in different colors or different shading and/or hatching in the 3D visual representation. The 3D visual representation may comprise all detected primary structures, or the 3D visual representation may comprise only a subset of the primary structures, which are contained in a specific class or in specific classes. In the latter case, the specific class or the specific classes to be visualized in the 3D visual representation may be selectable by a user.

According to an embodiment of the invention, the visualization of the primary structure is limited to at least one of the classes of implants, bones, bone fragments and/or reference bodies.

Reducing the number and class of primary structures to be visualized in the 3D visual representation according to the embodiment may support a user to focus on the essential information contained in the acquired 2D images and gathered in the 3D visual representation.

According to a further embodiment of the invention, the 3D visual representation is rotatable, such that the 2D images, which are represented as 2D slides in the 3D visual representation, can be viewed from different viewpoints. This may further support a spatial sense of a user.

According to an embodiment of the invention, the visualization of the primary structure may be based on a detection of a predetermined surgery step. Thereby, detection of a predetermined surgery step can be based on a number and a position of primary structures comprised in the 2D images.

Detection of a predetermined surgery step may be based on image processing of the 2D images comprising detection of various objects/devices in the 2D images. The detected objects/devices in the 2D images may be indicative of the step in the workflow during surgery. With the detection of the objects/devices in the 2D images it may be determined which step in the workflow is currently being performed by a user and which step(s) has(have) been performed before that.

More specifically, detection of a predetermined surgery step may comprise steps for identifying a current state of elements detected in the 2D image. Here, "current state" means first of all a position and orientation of the detected element. For instance, the position and orientation of the reference body can be determined due to the specific distribution of fiducial markers forming of being attached to the reference body. With respect to an instrument, like a gauge or a drill or a K-wire, the position may be detected in relation to the reference body and/or to an anatomical structure. A "current state" of an instrument may also include a deformation or bending of the instrument. Furthermore, a "current state" may indicate the appearance of the instrument and/or of an implant or sub-implant in the respective 2D projection image.

Based on the identified state of the detected elements, a state of progress of the procedure of e.g. fracture treatment may be determined. For example, information provided by a database with results of the previously performed may be compared to the position and number of elements in the 2D image, with the database including data defining each step out of a sequence of steps necessary to perform e.g. a fracture treatment procedure. For example, the steps may be defined in the database by the respective state of the elements which elements are involved in the particular step, so that information extracted from the 2-D projection image can be compared with information received from the database.

The step following the identified step out of the sequence of steps in the database may be used to provide or to derive information which step should be performed next.

According to an embodiment of the invention, the 2D images are X-ray images.

As stated above, the invention is not limited to X-ray images and images obtained with other imaging techniques than X-ray imaging may be used without departing from the scope of the invention.

A second aspect of the invention relates to a system for visualizing a bone. The system comprises a detection unit and a processing unit. The detection unit is configured to provide 2D images of the bone. Thereby, at least two 2D images should be taken from different imaging angles. The detection unit is further configures to detection outlines of a primary structure in the 2D images. Based on the outlines, the processing unit is configured to generate visual representations of the 2D images. The processing unit is further configured to arrange the visual representations of the 2D images as 2D slices in a 3D visual representation. The arrangement of the 2D slices in the 3D visual representation is based on the different imaging angels under which the 2D images are taken. It is intended that the 3D visual representation supports a spatial sense of a user.

A detection unit may be an imaging unit for providing images of an anatomical structure. For instance, a detection unit can be an X-ray imaging unit of a C-arm apparatus. A processing unit may be a processing device for processing data, such as a processing unit comprised in a computer. Such computer may be integrated together with its processing unit in a system for visualizing a bone according to the embodiment. The processing unit as part of a computer may also be an external device connectable to a detection unit, which is configured to provide images of an anatomical structure.

The detection unit of the imaging system may be comprised in an imaging apparatus such as a C-arm apparatus. Other examples of imaging systems providing a detection unit for providing 2D images may be one of an X-ray apparatus, an ultrasound imaging device or a magnetic resonance imaging device.

A third aspect of the invention relates to a computer program. The computer program is configured to perform any one or any combination of the above described method steps.

A fourth aspect of the invention relates to a computer readable medium, on which an above described computer program is stored. It may be considered as a gist of the invention to provide a 3D visual representation of a bone, which relies on a set of several 2D images only and supports a spatial sense of a surgeon without relying on a full 3D reconstruction of a region of interest. In other words, the 3D partial representation of the bone, bone fragment or implant provides sufficient information to allow the surgeon to use his or her imagination to fill in the missing data utilizing on the surgeon's knowledge of the region of interest which is based on the surgeon's experience and expertise. The surgeon knows from experience (or earlier images) the 3D form and shape of, for example, the femur of a patient. To reconstruct the position and orientation of the femur from an X-ray image he then does not need an image of the femur comprising the full shape and form of this bone, but only requires certain characteristic points (like an outline or the position of the head and the intertrochanteric line of the femur) may be enough for him. From his experience, and using his spatial imagination, he can reconstruct the 3D orientation of the femur by seeing the location of the characteristic points only. Hence, as a surgeon typically knows the actual shape/form of the objects depicted in the X-ray images, it is not necessary that the images contain the full information on the shape/form of the objects. An outline or characteristic points of a particular object can be enough to allow a skilled surgeon to complete, by his spatial imagination, the full object.

By using the method or the associated system according to the invention, a radiation dose to which a patient and a surgeon may be exposed during a surgery due to the number of images to be taken for obtaining a 3D visual representation of a region of interest may be significantly reduced. The method and the system may require fewer images because only 2D slices in a 3D visual representation are visualized and a full 3D reconstruction of the region of interest is not needed. Accordingly, method and system are therefore safer for patient and surgeon. In addition, computation power and computation time may be significantly reduced as no full 3D reconstruction is required.

DETAILED DESCRIPTION

Figure 1:
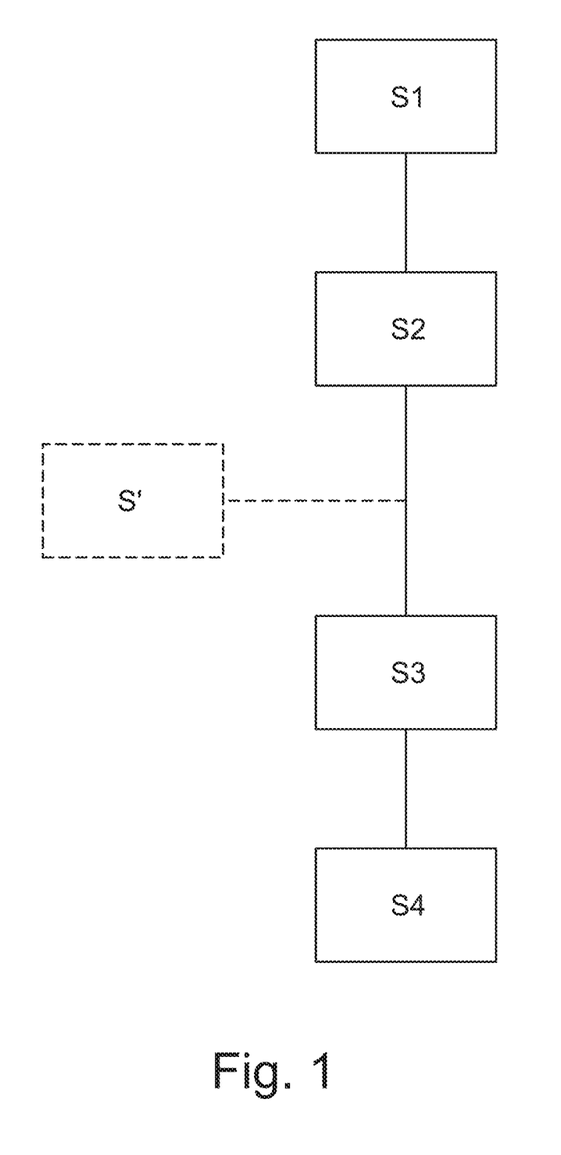
FIG. 1 shows a flow chart of steps of a method according to an embodiment of the invention.

The flow chart in FIG. 1 illustrates method steps performed in accordance with embodiments of the invention. It will be understood that the steps described may be major steps, wherein these major steps might be differentiated or divided into several sub-steps. Furthermore, there might be also sup-steps between the steps. Consequently, groups of steps may be related to a major aspect which may also be performed separately, i.e. independent from other steps or groups of steps.

It is noted that some steps are described as being performed "if necessary". This is intended to indicate that those steps may be omitted. It is in particular noted that a computer program element according to an embodiment of the invention may comprise sets of instructions to automatically recognize if a step is necessary or not, and to automatically proceed with the next actually necessary step.

With reference to FIG. 1, the exemplary method starts with providing 2D images of a region of interest in step S1. A region of interest may be a bone and the anatomic structures surrounding the bone. The images may be X-ray images. Alternatively, the images may be ultrasound images, magnetic resonance images or may be given by any other type of images acquired in medical diagnostics and/or therapy. In method step S2 outlines of a primary structure are detected in each of the 2D images of the bone. Thereby, an outline may be the shape of a primary structure in the respective image. Accordingly, an outline can be given by a contour line of the respective primary structure in the image. Detection of an outline can be carried out by e.g. comparing the grey-level value of neighbouring pixels or clusters of pixels in an image, thereby determining contour lines and in particular determining contour lines, which define the edge or boundary of a structure in the image, i.e. the boundary of a structure with respect to another structure depicted in the image.

A primary structure can be a bone and/or a bone fragment. Further, a primary structure can be given by an implant and/or a reference body. In context of the invention, a "primary structure" is a structure of interest during a surgical procedure. For instance, a femur or a hip bone, a corresponding implant and/or a bone screw can be primary structures in a 2D image provided in step S1 of a method according to the invention. Accordingly, a non-primary structure is a structure, which is of minor of no relevance in a specific surgical procedure. Tissue surrounding e.g. a hip bone, may, for instance be a non-primary structure, which can be of minor relevance for a surgeon during fixing of an implant in a hip bone.

In optional method step S', the detected primary structures can, if necessary, be classified into different classes, e.g. a class of implants, a class of bones and/or a class of markers or reference bodies. It may be possible that only those primary structures comprised in a specific selectable class or several selectable classes are visually represented in later method steps S3 and S4.

In method step S3, visual representations of each of the 2D images provided in step S1 are generated, based on the outlines detected in step S2. These visual representations of 2D images are subsequently arranged in a 3D visual representation in method S4. This is done by arranging the 2D images as corresponding 2D slices in a 3D visualisation. Each slice is arranged according to the angles under which the 2D image is taken. An example of such an arrangement is described in more detail in context of FIGS. 3A and 3B below.

Figure 2:
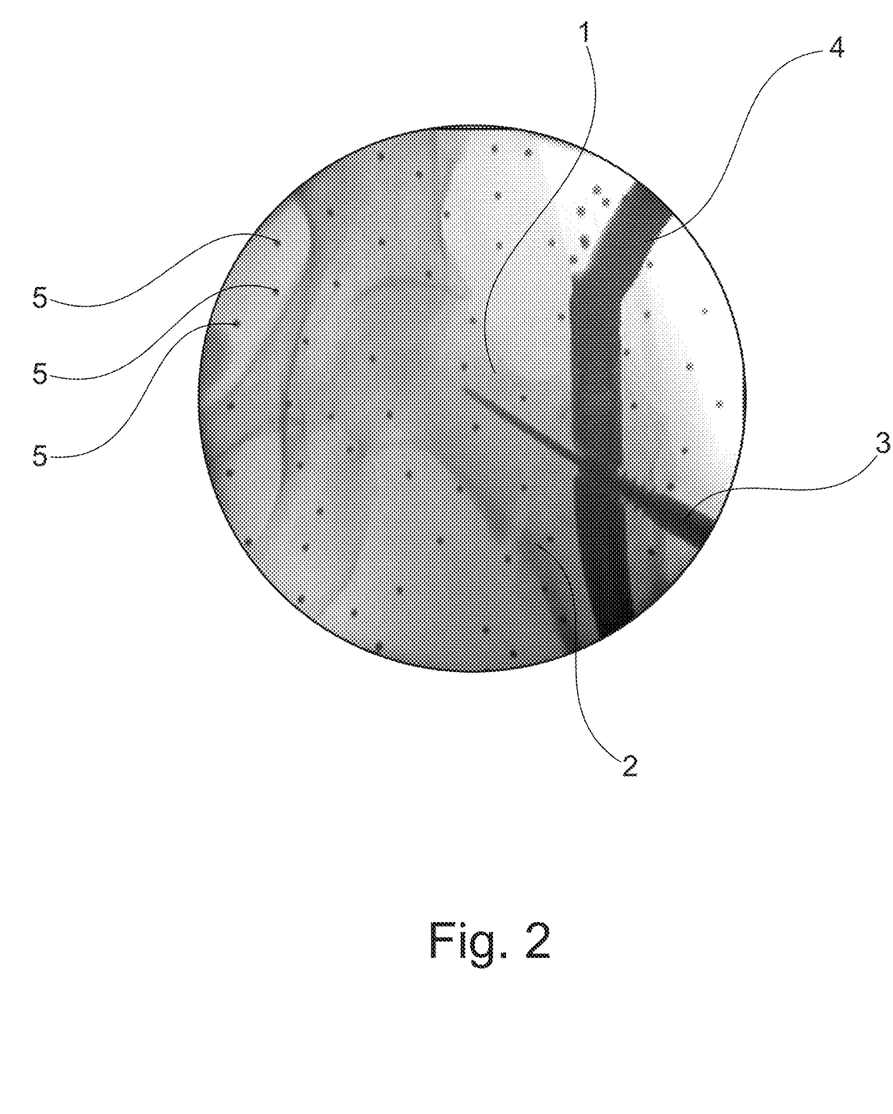
FIG. 2 shows an example of a monitor visualization of a 2D X-ray image according to an embodiment of the invention.

In FIG. 2, an example of a visualisation of a 2D image on a monitor or display is shown. The image comprises a bone 1 with a corresponding bone fragment or bone part 2. Further, an implant 3 is shown, as well as a drilling tool 4. A plurality of markers 5 is visible in FIG. 2. The latter markers allow determination of a spatial order and/or arrangement of the further structures visible in the image. With respect to FIGS. 6A and 6B a method is explained below that allows determination of a spatial arrangement from one single image.

Figure 3A:
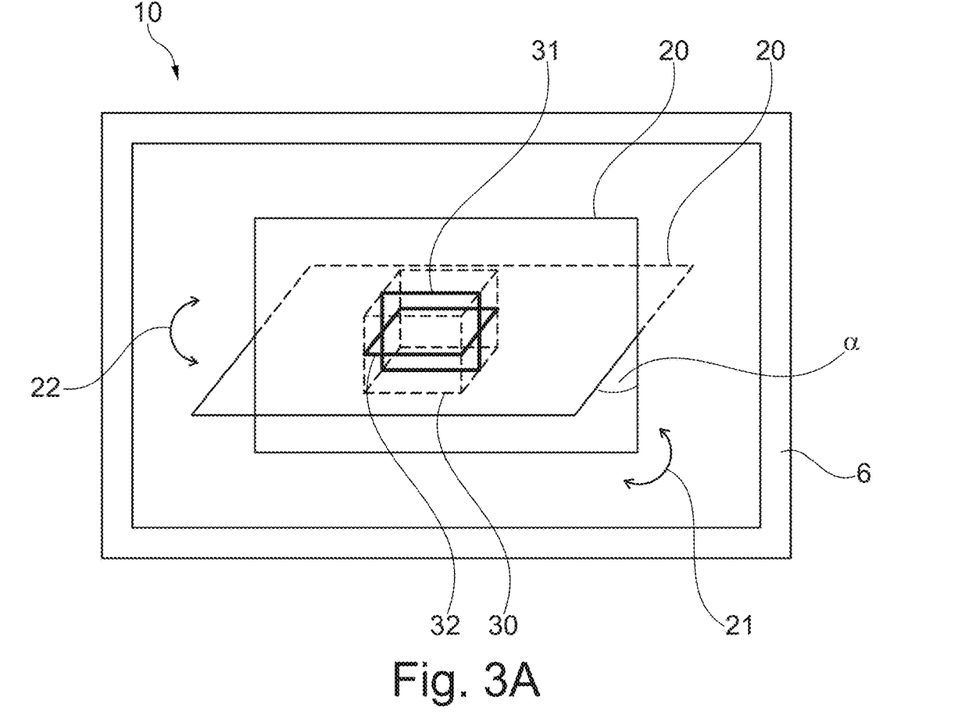
FIGS. 3A and 3B show schematic illustrations of a monitor visualization of a 3D visual representation according to an embodiment of the invention.

In FIG. 3A a schematic example of a 3D visual representation 10 displayed on a monitor or display 6 is shown. The 3D visual representation 10 comprises several 2D planes or 2D slices 20. On each 2D plane corresponding image information, i.e. information from a corresponding 2D image is displayed. Thereby, the 2D planes are arranged in the 3D visual representation reflecting the angles under which the 2D images were acquired. Accordingly, there is an angle α between the surface normal of the two planes in FIG. 3A.

The 3D visual representation may be rotatable. The possibility of rotating the representation, i.e. the representation of the planes in FIG. 3A is indicated by arrows 21 and 22. This possibility may further provide assistance to a surgeon, supporting his spatial sense to capture the 3D arrangement of a surgical area without the need to display all 3D information of the area but only slices or cuts through this area. Exemplarily, in order to put the idea across, a cuboid 30 is shown as a 3D structure in FIG. 3A. Only the solid lines 31, 32, which show the intersection of the cuboid 30 with the 2D planes, are displayed according to the invention. The dashed lines of the cuboid 30 are not shown, but only given in FIG. 3A to illustrate the idea.

Figure 3B:
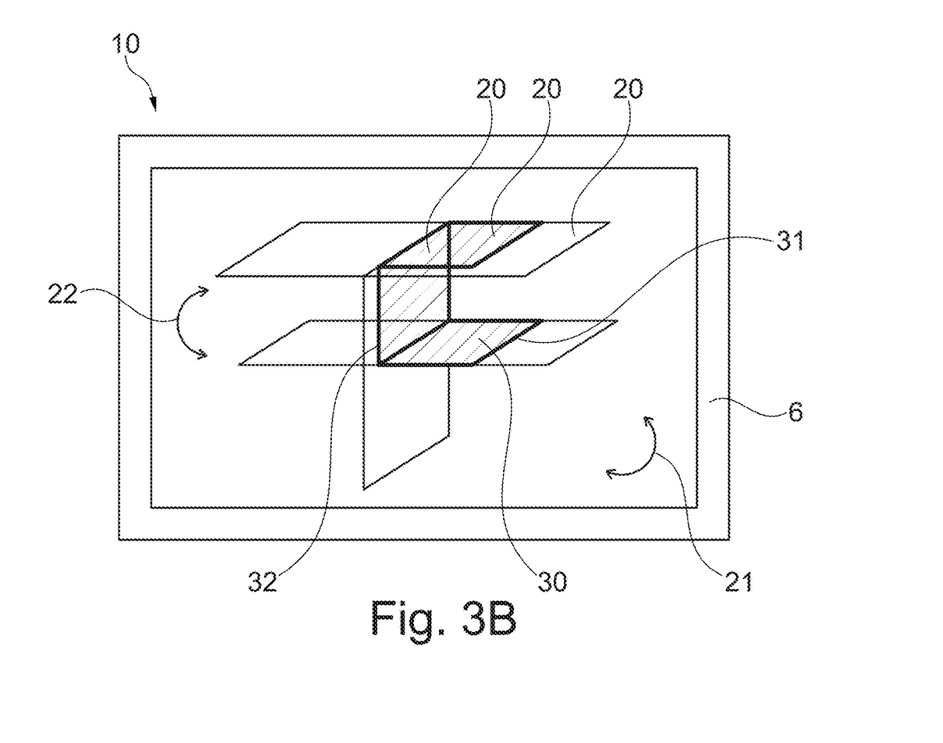

FIG. 3B shows a further schematic example of a 3D visual representation 10 displayed on a monitor 6. The 3D visual representation comprises several 2D planes, which are arranged in parallel to each other with a certain space between them. Arrows 21 and 22 indicate that the 3D visual representation may be rotatable. Further, the solid lines 31, 32 are contour lines of a cuboid 30, similar to the cuboid shown in FIG. 3A. However, in contrast to FIG. 3A, in FIG. 3B only the contours or the outline of the cuboid in the 2D planes 20 is shown.

Thus in FIG. 3A, the surgeon will know that the object visualised on the display (reference sign 6) is a cuboid (reference sign 30). However, the cuboid will not be displayed (the dashed lines will not be visible to the surgeon according to the invention). What will actually be shown on the display are the thick lines 31 and 32 only. Using his spatial sense, the surgeon can however reconstruct the position and orientation of the cuboid 30, although only the thick black lines 31 and 32 are shown on the display. In FIG. 3B a similar situation as in FIG. 3A is shown. Here the hashed planes are visualised on the display. The surgeon knows that these planes belong to a cuboid and can deduce, using his imagination (spatial sense), the position and orientation of the cuboid, relying on the depicted information.

Figure 4:
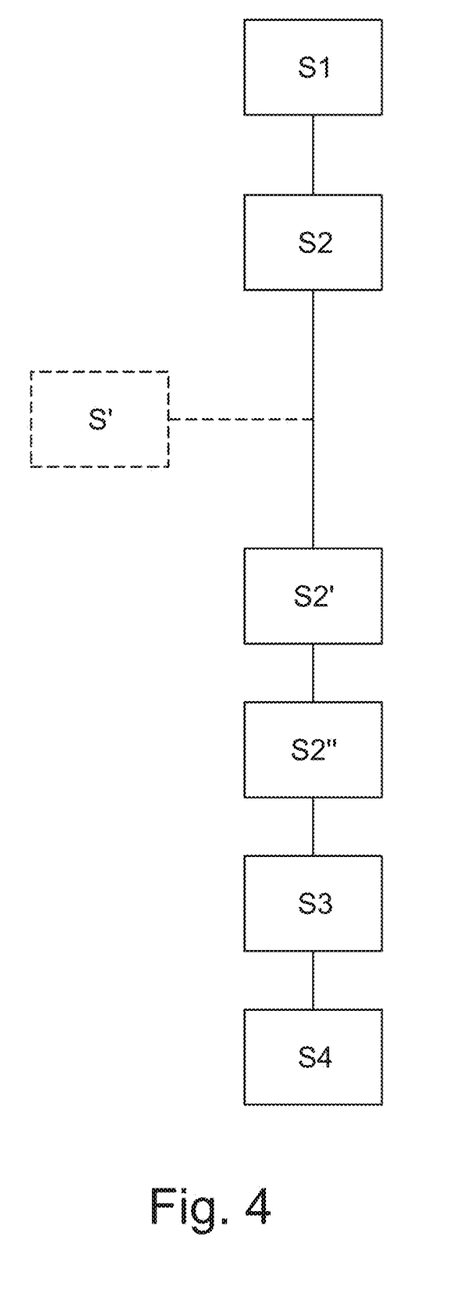
FIG. 4 shows another flow chart of steps of a method according to an embodiment of the invention.

The flow chart in FIG. 4 illustrates method steps performed in accordance with another embodiment of the invention. In method step S1, 2D images are provided and in each of these images outlines of at least one primary structure are detected in subsequent method step S2. Optionally, the detected primary structures can then be classified into one of the classes of implants, bones, bone fragments, reference bodies and/or markers.

In the subsequent step S2', at least three markers are detected in each of the 2D images. Based on the position and angles under which these markers are detected in each of the 2D images, a spatial arrangement of the primary structures in each 2D image is determined. An example, how such determination may be performed, is given below with reference to FIGS. 6A and 6B. After the spatial arrangement of the primary structures is determined, a visual representation of the 2D images is generated in subsequent method step S3. The latter visual representation of all or a part of the 2D images is arranged in a 3D visual representation as 2D slices or 2D planes.

Figure 5:
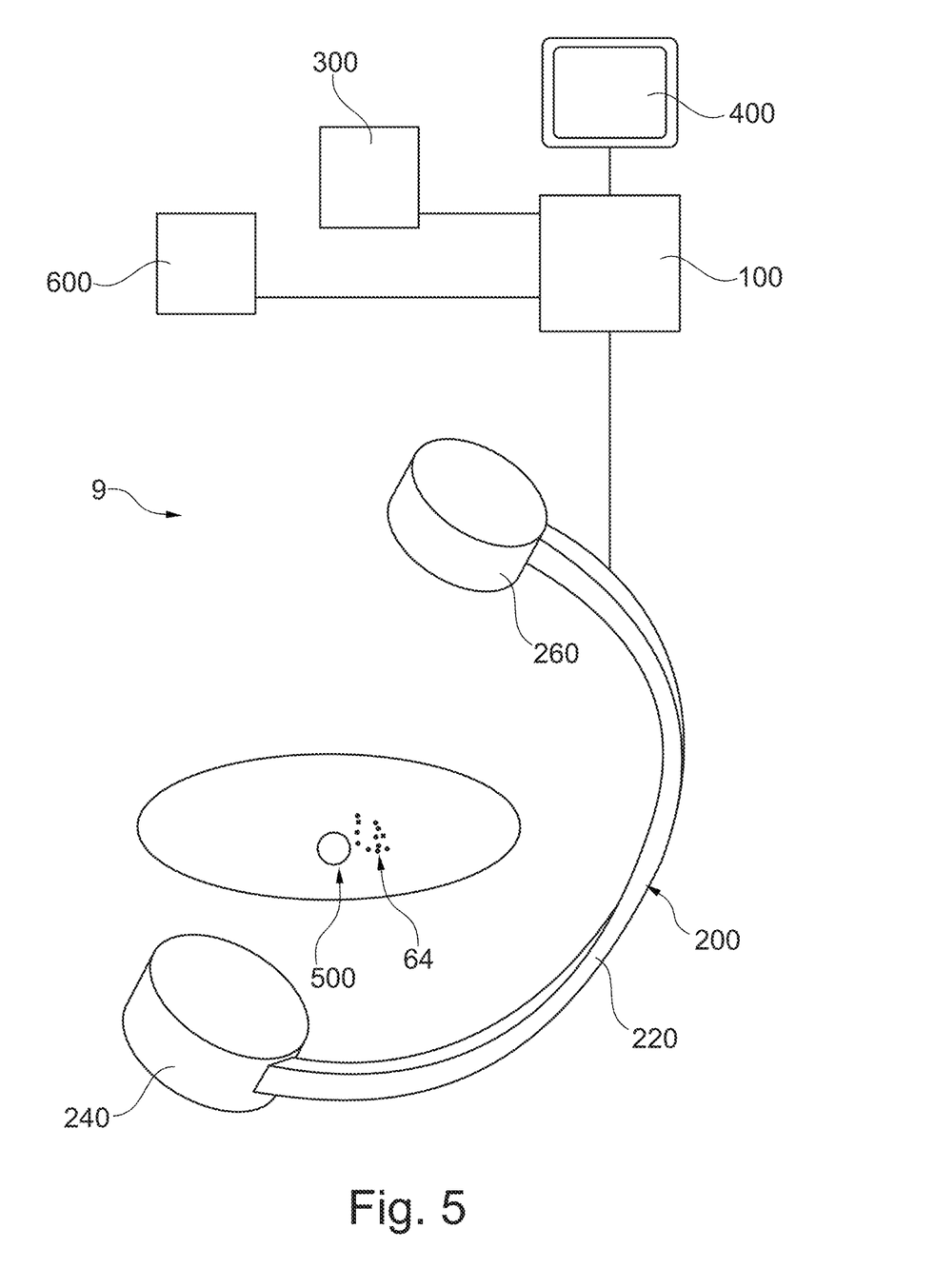
FIG. 5 shows a schematic illustration of a system according to an embodiment of the invention.

FIG. 5 shows an exemplary embodiment of a system 9 according to an embodiment of the invention. Substantially, necessary for performing the steps of the method, a processing unit 100 is part of the device.

An exemplary imaging device or imaging unit 200 includes an X-ray source, and an X-ray detector 260, wherein these two units are mounted on a C-arm 220.

Furthermore, the system 9 in FIG. 5 includes an input unit 300, by means of which for example an intended imaging direction may be manually entered. Further, a user can input structures, which shall be considered as primary structures in the images. Also shown is a connection to a database 600, located for example in a network. The database 600 may comprise information regarding anatomical structures, for example from 3D scans of different anatomical structures, so that the imaged anatomical structure may be compared with this information so as to determine or identify specific anatomical structures. The database may further comprise information regarding a sequence of necessary and/or possible steps of a surgical procedure. Further, the database can comprise a storage comprising at least one or a series of earlier acquired reference images. It is noted that it is also possible to automatically determine the progress of the surgical procedure based on detectable aspects in an x-ray image, wherein such aspects may be in instrument and/or implant.

Finally, there is an indication in FIG. 5 of an anatomical structure of interest 500 as well as of a reference object 64 formed by a plurality of radiopaque spheres. Within said anatomical structure, for example a bone of a patient may be located which may be subject to the described procedures.

Figure 6A:
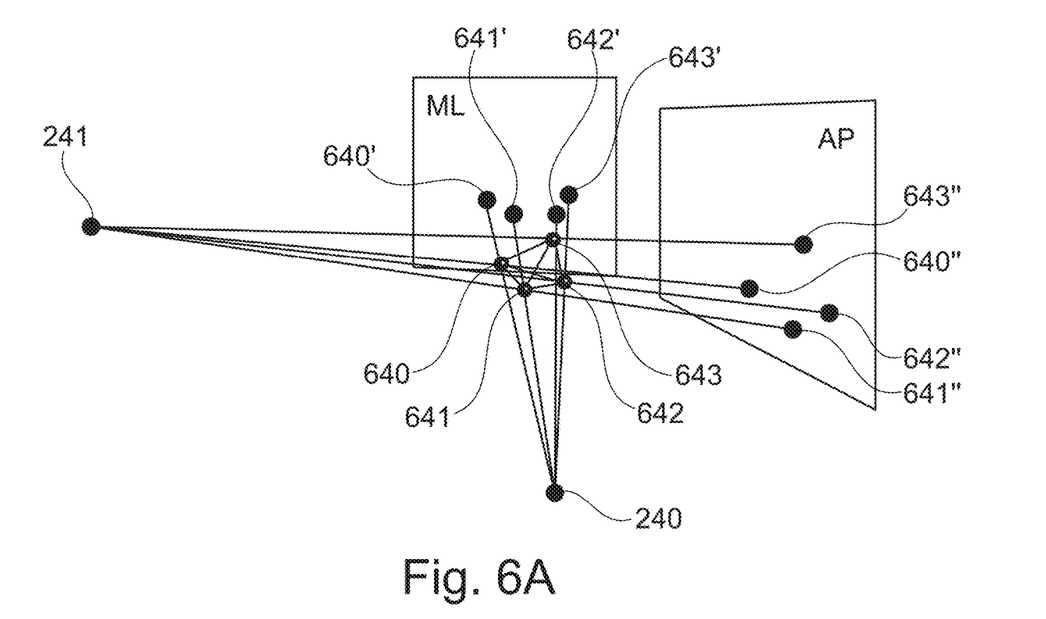
FIGS. 6A and 6B are schematic visualizations regarding a projection of a reference body.
Figure 6B:
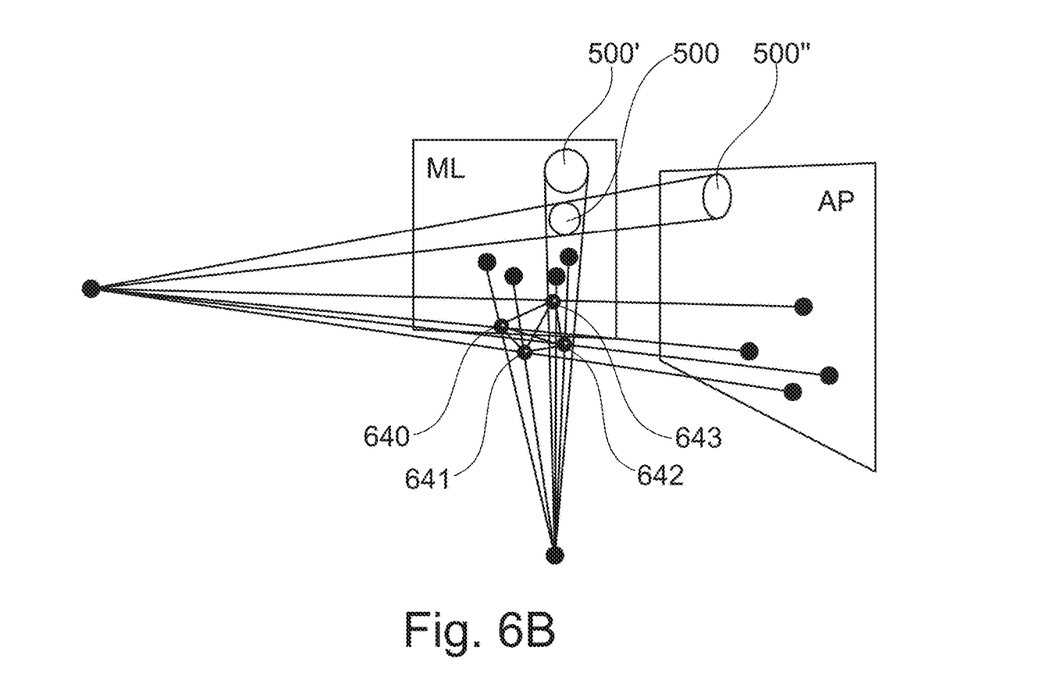

With reference to FIGS. 6A and 6B, a method to determine a spatial arrangement of objects in a 2D image is explained in the following.

FIG. 6A shows a reference body formed, in the example, by four spheres 640, 641, 642, 643 being arranged in space in a predetermined way. Further shown are lines representing x-ray beams emitted by an x-ray source 240, 241, respectively. Each line ends on one of the projection surfaces denoted as AP (anterior-posterior) or ML (medio-lateral). On the projection surface ML, the spheres of the reference body form a first pattern of projection points 640', 641', 642' and 643', and on the projection surface AP, the spheres form a second pattern of projection points 640", 641", 642" and 643". As can be easily seen, the first pattern on the surface ML differs from the second pattern on the surface AP. A skilled person will appreciate that it is possible to arrange spheres of a reference body in three-dimensional space such that a unique projection pattern will be achieved for each projection direction. Consequently, it is possible to determine the imaging direction, based on the detected projection pattern, and to determine the actual orientation of the reference body in space in relation to the imaging device. Furthermore, as the beams follow a fan angle, the spatial position, i.e. the distances of the references body to the x-ray source and the x-ray detector, respectively, can be calculated based on measured distances of the projection points. In fact, it is merely a matter of geometry to calculate the actual position and orientation of the reference body based on a single projection of the same.

With the reference body as a "spatial anchor", it is also possible to determine an actual position and orientation of an anatomical structure based on a single x-ray image, as schematically illustrated in FIG. 6B. Here, a projection of a head 500 of a femur, i.e. of a ball head is shown on each of the projection surfaces, wherein the relation of the projection 500' to the projections of the reference body on the surface ML differs from the relation of the projection 500" to the projections of the reference body on the surface AP. This illustrates that the projections of the reference body and the relation to the anatomical structures in the projection image are unique for each imaging direction. Consequently, the spatial position and orientation of the reference body can be determined and also the spatial position and orientation of the anatomical structure in the vicinity of the reference body, based on one x-ray image.

While embodiments have been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practising the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited and mutually different dependent claims does not indicate that a combination of these measures cannot be used to advantage. The computer program may be stored/distributed on a suitable medium such as an optical storage medium or a solid-state medium supplied together with or as a part of another hardware, but may also be distributed in other forms, such as via the Internet or other wired or wireless telecommunication systems. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for visualizing a bone, comprising:
    providing a plurality of 2D images of the bone, wherein at least two of the 2D images are taken at different imaging orientations with respect to the bone,
    detecting outlines of a primary structure in the 2D images of the bone,
    generating visual representations of the 2D images based on the outlines, and
    displaying the visual representations of the 2D images simultaneously on respective 2D planes in a 3D visual representation, wherein at least two of the 2D planes are oriented in the 3D visual representation so as to intersect at an intersection angle, the at least two of the 2D planes corresponding to the at least two of the 2D images taken at different imaging orientations, and the intersection angle corresponding to an angle defined between the respective imaging orientations of the at least two 2D images.

2. The method according to claim 1, wherein the primary structure is at least one of a bone and a bone fragment.

3. The method according to claim 1, wherein the primary structure is at least one of an implant and a reference body.

4. The method according to claim 1, further comprising the steps of:

detecting at least three markers in the 2D images, wherein a marker is one of a reference body, a part of a reference body, an implant or a bone shape, and determining a spatial arrangement of the primary structure based on the position of the at least three markers, wherein the step of arranging the visual representation of the 2D images in the 3D visual representation is based on the determined spatial arrangement.

5. The method according to claim 1, further comprising the step of:

classifying the primary structure into a class of implants, a class of bones, a class of bone fragments and/or a class of reference bodies, wherein the step of arranging the visual representation of the 2D images in the 3D visual representation is based on the classification of the primary structure.

6. The method according to claim 5, wherein the visualization of the primary structure is limited to at least one of the classes of implants, bones, bone fragments and/or reference bodies.

7. The method according to claim 1, wherein the 3D visual representation is rotatable showing the visual representations of the 2D images from different viewpoints.

8. The method according to claim 1, wherein the visualization of the primary structure is based on a detection of a predetermined surgery step, wherein detection of the predetermined surgery step is based on a number and a position of primary structures in the 2D images.

9. The method according to claim 1, wherein the 2D images are X-ray images.

10. A non-transitory computer readable medium encoded with a computer program, which, when executed by a processor, performs the method steps according to claim 1.

11. The method according to claim 1 wherein only two 2D images of a femur are used with the two 2D images taken at angles of at least 15° from one another.

12. The method according to claim 11 wherein the two 2D images are x-ray images.

13. The method according to claim 2 wherein the primary structure is a femur or a hip bone.

14. The method according to claim 1 wherein the 2D planes in the 3D visual representation are arranged such that a region defined between the at least two of the 2D planes intersecting at the intersection angle is represented as empty space.

15. The method according to claim 1 wherein a plurality of the 2D planes are arranged in the 3D visual representation as parallel to and offset from one another with an empty space therebetween.

16. A system for visualizing a bone, comprising:

a detection unit configured to receive a plurality of 2D images of the bone, wherein at least two of the 2D images are taken at different imaging orientations with respect to the bone, and the detection unit being configured to detect outlines of a primary structure in the 2D images of the bone, and a processing unit configured to generate visual representations of the 2D images based on the outlines, and the processing unit being configured to arrange the visual representations of the 2D images simultaneously on respective 2D planes in a 3D visual representation for display on a monitor, wherein at least two of the 2D planes are oriented in the 3D visual representation so as to intersect at an intersection angle, the at least two of the 2D planes corresponding to the at least two of the 2D images taken at different imaging orientations, and the intersection angle corresponding to an angle defined between the respective imaging orientations of the at least two 2D images.

17. The system according to claim 16 wherein the processing unit is configured to arrange the 2D planes in the 3D visual representation such that a region defined between the at least two of the 2D planes intersecting at the intersection angle is represented as empty space.

18. The system according to claim 16 wherein the processing unit is configured to arrange a plurality of the 2D planes in the 3D visual representation as parallel to and offset from one another with an empty space therebetween.

* * * * *